United States Patent
Joshi et al.

(10) Patent No.: US 6,787,008 B2
(45) Date of Patent: Sep. 7, 2004

(54) HYDROGEN GENERATING CELL WITH CATHODE

(75) Inventors: Ashok V. Joshi, Salt Lake City, UT (US); Strahinja K. Zecevic, Salt Lake City, UT (US)

(73) Assignee: Microlin, L.C., Salt Lake City, UT (US)

( * ) Notice: Subject to any disclaimer, the term of this patent is extended or adjusted under 35 U.S.C. 154(b) by 19 days.

(21) Appl. No.: 10/115,273

(22) Filed: Apr. 2, 2002

(65) Prior Publication Data

US 2003/0082415 A1 May 1, 2003

Related U.S. Application Data

(60) Provisional application No. 60/335,050, filed on Oct. 30, 2001.

(51) Int. Cl.[7] .............................. C25B 9/00; C25C 7/00; C25D 17/00
(52) U.S. Cl. ...................... 204/252; 204/263; 204/266; 204/282; 204/295
(58) Field of Search ................................ 204/252, 263, 204/266, 282, 295

(56) References Cited

U.S. PATENT DOCUMENTS

| | | | |
|---|---|---|---|
| 3,894,538 A | 7/1975 | Richter | |
| 4,023,648 A | 5/1977 | Orlitzky et al. | |
| 4,189,526 A | * 2/1980 | Cretzmeyer et al. | .......... 429/13 |
| 5,968,325 A | 10/1999 | Oloman et al. | |
| 6,042,957 A | 3/2000 | Oltman | |
| 6,087,030 A | 7/2000 | Collien et al. | |
| 6,461,761 B1 | * 10/2002 | Moy et al. | .................. 429/127 |

* cited by examiner

*Primary Examiner*—Wesley A. Nicolas
(74) *Attorney, Agent, or Firm*—Factor & Lake, Ltd.

(57) ABSTRACT

A storage stable hydrogen cell comprising an anode cap subassembly, cathode can subassembly, and a grommet is disclosed. For one embodiment the cathode in the cathode can subassembly is configured for contact with the electrolyte. The cathode is hydrogen permeable and substantially impermeable to $O_2$, $CO_2$ and water. In turn, the cathode can preclude the passage of $O_2$, $CO_2$ and water into and out of the cell, and simultaneously can facilitate the permeation of hydrogen through at least one aperture in the cell. In another embodiment, a commercially available Zn-air cell is converted into storage stable $H_2$ cells by sealing a membrane structure around the apertures of the Zn-air cell. Such membrane precludes the passage of $O_2$, $CO_2$ and water into and out of cell but allows the passage of hydrogen generated in the cell through the aperture of the cell and through the membrane.

15 Claims, 6 Drawing Sheets

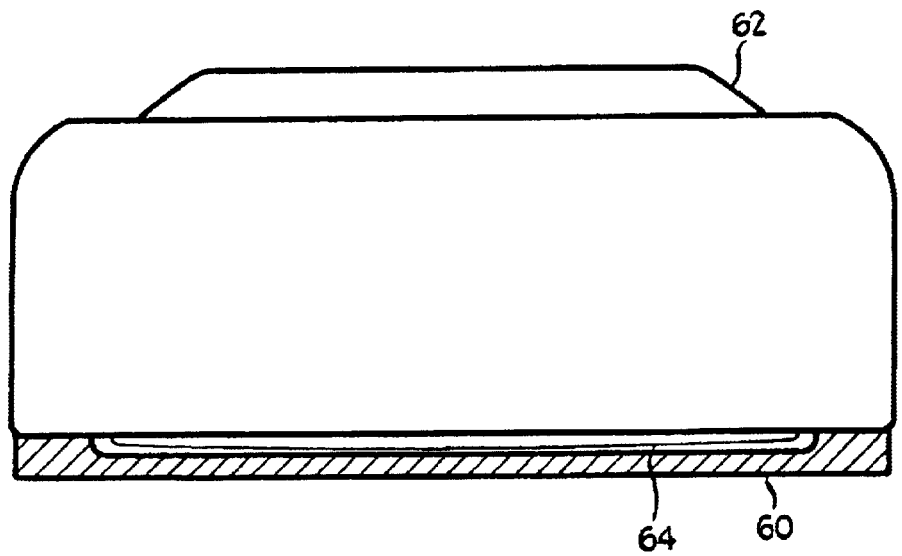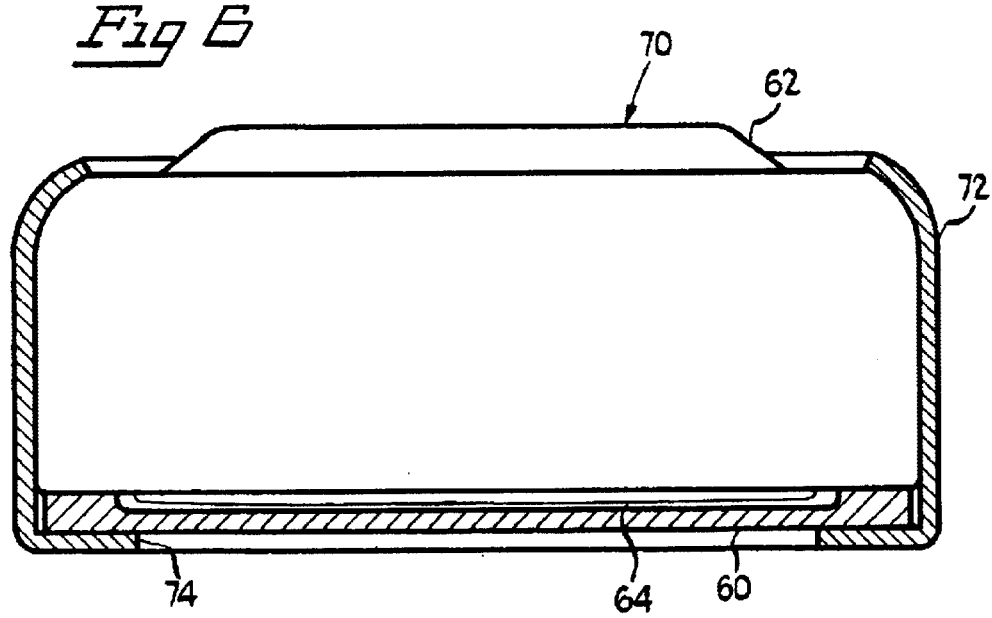

HYDROGEN GENERATING CELL WITH CATHODE

This application claims the benefit of Provisional Application No. 60/335,050, filed Oct. 30, 2001.

BACKGROUND OF THE INVENTION

1. Field of the Invention

The invention relates in general to storage stable hydrogen electrochemical gas generating cells, and, more particularly, to improved cathode related structures for hydrogen generating cells. The invention also relates to converting commercially available Zn-air cells to efficient and storage stable hydrogen generating cells in which commercial Zn-air cells are packaged with a membrane of the type that precludes the passage of $O_2$ and water in and out of the cell but allows hydrogen gas out of the cell. The invention further relates to a system wherein the commercial Zn-air cell is converted to a storage stable $H_2$ gas-producing cell.

2. Background Art

Various devices have been utilized for dispensing fluids, where the fluids are dispensed over an extended period of time at a predictable substantially constant rate. One such device for dispensing fluid, as shown in FIG. 1, is based on using an electrochemical gas generating cell in which hydrogen gas is electrochemically generated to pressurize a gas chamber which, in turn, dispenses the fluid from the device.

A prior art construction of a hydrogen-generating cell is of a Zn-air type cell, shown in FIG. 2. A Zn-air cell typically utilizes zinc as the anode, a carbon based cathode and an alkaline solution as the electrolyte. The anode cap subassembly is comprised of a Zn alloy, an electrolyte, and the cap. The cathode can subassembly is comprised of a carbon-based porous electrode, a separator, and the can, all of which are crimped together using a plastic grommet as an insulator.

Various prior art patents describe the construction of such cells. For example, U.S. Pat. No. 3,894,538, issued to Richter and U.S. Pat. No. 4,023,648, issued to Orlitzky disclose metal-air cells for generating hydrogen as a motive force. Similarly, Winsel, U.S. Pat. No. 5,242,565 and Winsel EP 1013296 both disclose use of a conventional Zn-Air cell for generating hydrogen or oxygen as a motive force. However, none of these references utilize a cathode structure which is hydrogen permeable and, substantially impermeable to preclude ingress of oxygen, carbon dioxide And water (moisture) into and out of the associated cell. Although such prior art cells can be utilized as hydrogen generative cells, they are very inefficient and have short storage life in their active state mainly due to interference of $O_2$ and $CO_2$ as well as loss of moisture through the cathode.

Accordingly, it is an object of the present invention to provide for an improved cell construction, which overcomes the shortcomings of the prior art. It is also an object of the present invention to convert commercially available Zn-air cells and prior art hydrogen generative cells into storage stable and efficient hydrogen gas generative cells by attaching a non-porous membrane to the cathodic side of the outer housing so that $O_2$ and $CO_2$ are prevented from entering the cathode while water vapor is simultaneously prevented from escaping the cell through the cathode. Furthermore, it is an object of the present invention to provide a device in which hydrogen is permitted to escape from the cell.

SUMMARY OF THE INVENTION

One embodiment of the invention comprises a galvanic cell, which includes an anode cap subassembly comprising a metal anode, electrolyte, a cathode can subassembly, a micro-porous separator, and a sealing grommet. The anode may comprise zinc, lead, iron, magnesium, aluminum and mixtures and alloys thereof.

The cathode can subassembly is further comprised of a cathode that is permeable to hydrogen, but substantially impermeable to $O_2$, $H_2O$ and $CO_2$. In a preferred embodiment, the cathode comprises at least one of a non-porous dense electrically conducting polypropylene, a non-porous composite of carbon, PTFE (such as TEFLON(®), manufactured by E. I. du Pont de Nemours and Company), and FEP foil; a palladium foil, an iron titanium foil, an iron magnesium foil, as well as metallic membranes of one or more of palladium, nickel, titanium, and, non-porous polymers, and composites of ceramics and palladium. The cathode materials will not allow $O_2$, moisture and $CO_2$ to permeate in and out of the cell but will allow hydrogen to escape the cell.

In another preferred embodiment, the cathode includes a graded porosity. In such an embodiment, the cathode comprises a graded porosity from a highly porous structure (50% pores with a pore size of 1 micron or greater) to a non-porous structure along its thickness. In this case, a carbon Teflon PTFE composite with graded porosity is cladded to non-porous FEP foil. This cathode structure exhibits the required properties for highly efficient hydrogen generative systems that warrant that the cathode is hydrogen-permeable but impermeable to $O_2$, $CO_2$, and $H_2O$.

In another preferred embodiment, the cathode comprises a nonporous conductive cathode.

In a preferred embodiment, the cathode comprises a non-porous conductive polymer. In one such preferred embodiment, the polymer comprises at least one of conductive PTFE and conductive polypropylene or conductive polyethylene.

In a preferred embodiment, the at least one aperture of the outer shell comprises a plurality of apertures, each of which has a diameter of less than about 5 microns.

In another aspect of the invention, the invention comprises a system comprising a commercial Zn-air cell or prior art galvanic electrochemical $H_2$ gas generating cell and a membrane. The galvanic electrochemical $H_2$ gas-generating cell includes at least one aperture for releasing gas. The membrane is associated with the at least one aperture. The membrane is hydrogen permeable and substantially impermeable to $O_2$, $CO_2$ and water, to, in turn, preclude the passage of $O_2$, $CO_2$ and water into and out of the cell, and to facilitate the permeation of hydrogen through the at least one aperture.

The commercial Zn-air cells as well as prior art hydrogen generating electrochemical cells use a gas permeable porous cathode through which all the gases including $O_2$, $H_2O$, and $CO_2$ can permeate. This permeation results in $O_2$ and $CO_2$ interference and water loss during operation, and in turn, low efficiency and short storage life during the hydrogen generating mode. The present embodiment of the invention describes the construction and method of converting commercial Zn-air cells and prior art hydrogen cells to more efficient hydrogen generating cells by incorporating such cells so that the cathode is not exposed to outside $O_2$, $H_2O$, and $CO_2$, but allows generated hydrogen to escape.

In one preferred embodiment, the membrane is electrically conductive. In one such preferred embodiment, the membrane is selected from the group consisting of: electrically conductive non-porous polypropylene; sintered composite of carbon, PTFE, and FEP foil; palladium foil, iron titanium foil, iron magnesium foil, as well as metallic membranes of one or more of palladium, nickel, titanium, and, non-porous polymers, and composites of ceramics and palladium.

In another preferred embodiment, the membrane is electrically insulative. In one such preferred embodiment, the membrane comprises at least one of polypropylene and PTFE.

In a preferred embodiment, the system further includes an outer casing assembly encircling a portion of the membrane and at least a portion of the cell. In one such preferred embodiment, the outer casing assembly further comprises a cap, a can and an isolation grommet positioned between the can and the cap.

The present invention is also directed to a method for generating hydrogen using a zinc anode-based electrochemical cell comprising the steps of associating an electrically conductive circuit with a storage-stable hydrogen generating cell, with one end of the circuit connected to a anode subassembly of the cell, and the other end of the circuit connected to a cathode subassembly of the cell having a non-porous cathode, generating hydrogen within the cell electrochemically, and selectively releasing hydrogen from the cell through the non-porous cathode, while simultaneously preventing the passage of oxygen and water into or out of the cell.

BREIF DESCRIPTION OF THE DRAWINGS

FIGS. 5–8 are cross-sectional views of various structures related to conversion of Zn-air cells to hydrogen generating cells of the present invention;

DETAILED DESCRIPTION OF THE DRAWINGS

Figure 1:
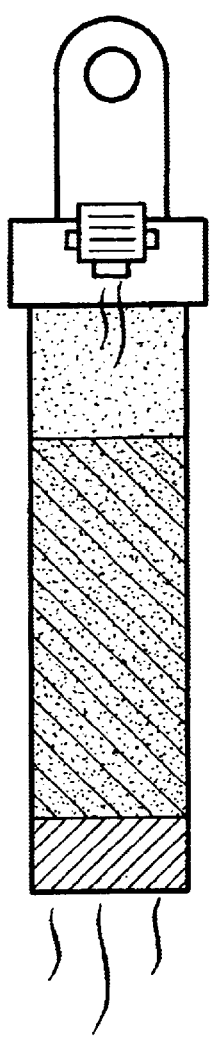
FIG. 1 is a prior art fluid delivery device using a gas-generating cell.

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

Figure 3:
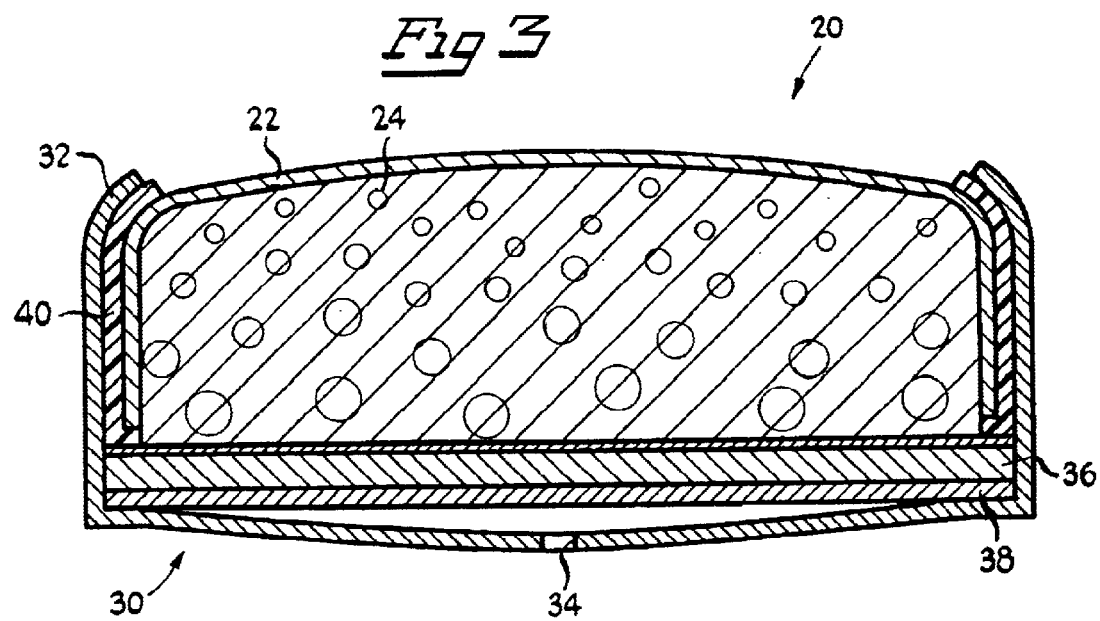
FIG. 3 is a cross-sectional view of an $H_2$ generating cell of the present invention.

Zinc anode-based electrochemical cell, or "button cell" 10 is shown in FIG. 3, as comprising zinc-based anode subassembly 20, non-porous cathode-based cathode subassembly 30, and grommet 40. Zinc based anode subassembly 20 comprises metal cap 22 containing a Zn alloy, and alkaline electrolyte 24. Non-porous cathode-based cathode subassembly 30 comprises can 32, and at least one aperture 34. Cathode subassembly 30 is further comprised of non-porous cathode structure 36 and separator 38. Although the present description will be with respect to a zinc based anode, it will be understood to those having ordinary skill in the art that other metals, such as zinc, lead, iron, magnesium, aluminum and mixtures and alloys thereof, can likewise be used. Accordingly, the present invention should not be limited to a zinc air cell.

Non-porous cathode structure 36 comprises several possible embodiments, as illustrated in FIGS. 4–8. The various non-porous cathode structures shown include standard cathode structures of commercial Zn-air cells with additional outside enclosures so as to render the cathodes hydrogen-permeable, but impermeable with respect to oxygen, $CO_2$ and water. Such cathode structures may take many forms, but preferably include membranes formed from materials such as non-porous, dense polypropylene, palladium foil, iron titanium foil, iron magnesium foil, and sintered composites of carbon, PTFE, and FEP foil. Of course, other structures and materials which exhibit the foregoing properties of permeation are likewise contemplated for use, including, but not limited to other metallic membranes of palladium, nickel, titanium, non-porous polymers, composites of ceramics and palladium, as well as combinations and mixtures thereof.

One particularly useful embodiment involves a conductive non-porous polypropylene or PTFE cathode (or other non-porous conductive polymer cathode). In that embodiment, the polypropylene or PTFE cathode is permeable to hydrogen, but impermeable to $O_2$ and to water/moisture. In operation of such an embodiment, hydrogen is generated on the conductive portion of the conductive polymer and then permeated through the polymer material.

Figure 4:
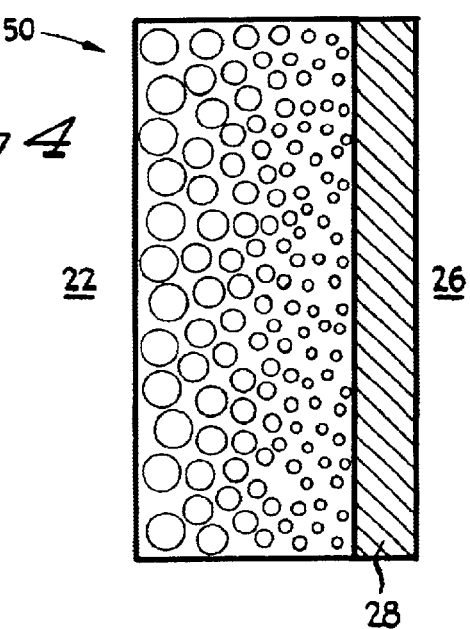
FIG. 4 is a cross-sectional view of a cathode with graded porosity of present invention.

One of the possible structures of cathode 36 is shown in FIG. 4 as comprising a graded cathode 50. Graded cathode 50 comprises an electrode having a graded porosity such that it is most porous at the side facing the electrolyte 22 and substantially non-porous at the side facing the gas side 26. Such a graded electrode can be achieved by varying the catalyst material to density material ratio throughout the thickness in order to increase/decrease permeation of materials accordingly. The density material to catalyst material ratio may then eventually be increased so that at least a portion of graded cathode 50 is non-porous.

Additionally, it may be desirable to clad a non-porous film 28 to the porous cathode composite, as can also be seen in FIG. 4. The catalyst material of such an embodiment generally comprises graphite, active carbon, Reney nickel or other metals suitable for hydrogen generation such as for instance platinum or palladium. Of course, other materials are contemplated for the catalyst. In addition, materials such as PTFE and polypropylene, among others, are contemplated for use as the density material.

In another embodiment of the invention, the cathode may comprise a completely non-porous cathode. Such a cathode is preferably a sintered composite of polymer and conductive material. The thickness of such a non-porous composite cathode is at least about 0.001 inches. Such a cathode is obtained by way of sintering the composite of polymer and conductive material under pressure and heat. For example, polypropylene powder or PTFE powder is mixed with metals or carbon and then sintered under pressure.

Referring again to FIG. 3, a grommet 40 (preferably of nylon) electrically isolates the anode cap 22 from the cathode can 32. The cathode can 32 is then crimped around the grommet assembly forming a seal. The cathode can 32 is comprised of nickel-plated steel, and is in direct electrical contact with the cathode 36. The can 32 has at least one aperture 34 to permit passage of gasses in or out of the cell. In one embodiment, aperture 34 may comprise a plurality of apertures.

As shown in FIG. 5, the advantages of the above-described cathode structure may be provided to commercially available Zn-air cells by including membrane 60 to Zn-air cell 62 so as to provide a storage stable $H_2$ gas generating system. Membrane 60 includes the above-described properties of being hydrogen permeable while being substantially impermeable to $O_2$, $CO_2$ and water. The membrane may be either conductive or insulative. The materials for membrane 60 may comprise those materials identified above and, in addition, non-conductive non-porous polypropylene and PTFE. By way of example, as shown in FIG. 5, membrane 60 may be positioned in a gas-tight engagement with a lower surface 64 of the Zn-air cell 62 (i.e., the cathode can).

Figure 7:
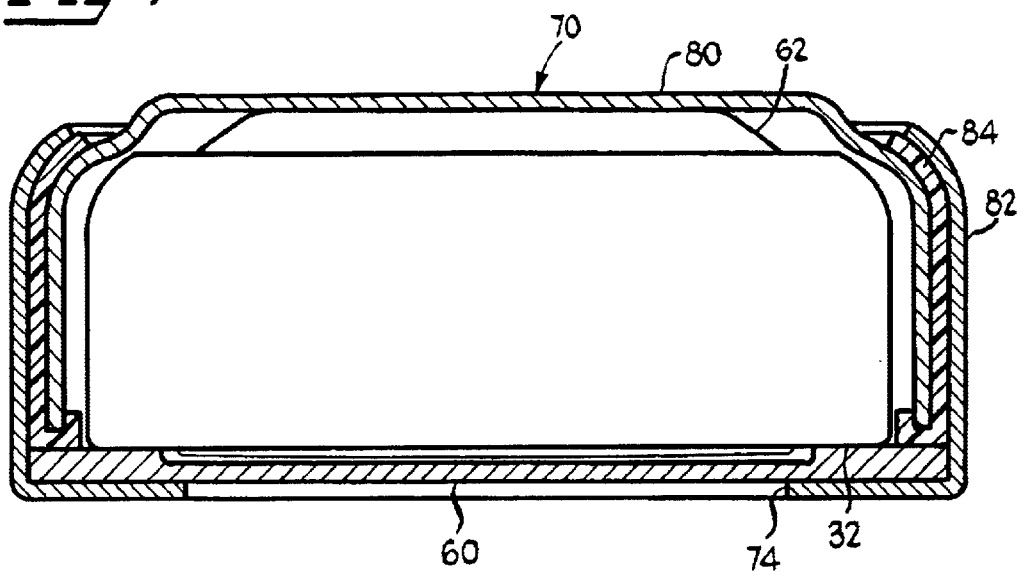
Figure 8:
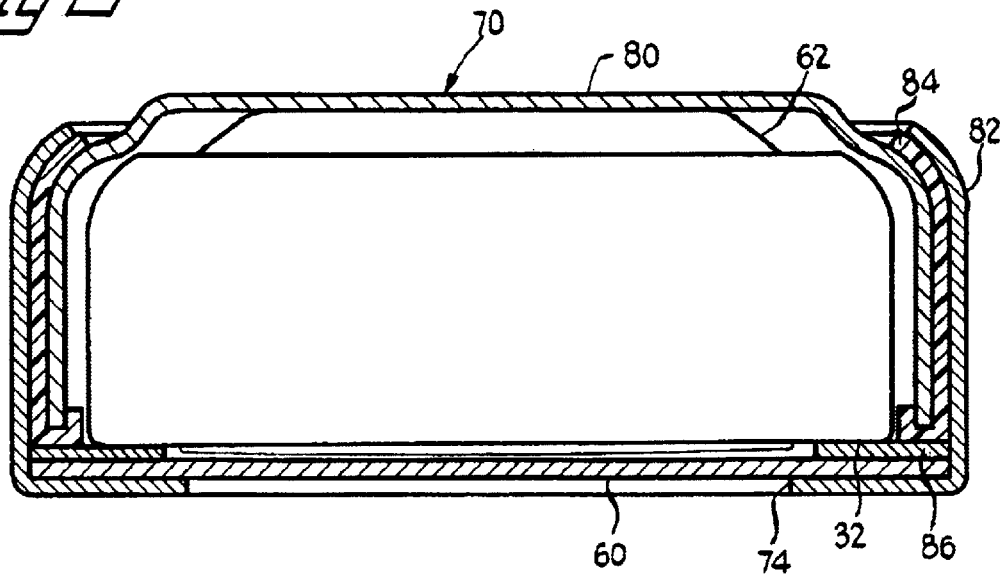

The embodiments of FIGS. 6–8 are all capable of use in association with conventional Zn-air cells, so as to provide the advantages of membrane 60 thereto. Specifically, as shown in FIG. 6, the Zn-air cell 62 may further be supplemented with outer casing assembly 70, which includes metal casing can 72. Metal casing can 72 includes lower opening 74 and may comprise a conductive metal material. In such an embodiment, membrane 60 may be positioned in a gas-tight engagement with lower surface 64 of the conventional cell 62. Subsequently, the entire cell 62 with membrane 60 may be positioned within metal casing can 72 such that electrical connectivity is achieved between the conventional cell and metal casing can 72. In addition, a portion of membrane 60 remains exposed within lower opening 74. Once properly assembled, the metal casing can 72 is crimped much like cathode can 10 of FIG. 3.

In another embodiment of the invention, as shown in FIG. 7, the conventional cell may be further supplemented with another embodiment of outer casing assembly 70. In this embodiment, assembly 70 includes cap 80, can 82 and isolation grommet 84. In such an assembly, a standard zinc-air cell 62 is first positioned within cap 80. Thereafter, isolation grommet 84 is extended around cap 80. Next, membrane 60 is positioned such that membrane 60 contacts both the isolation grommet 84 and the cathode can 32 of the cell. The cell 62 is positioned within can 80, wherein the can 82 is crimped to the isolation grommet 84 and the cap 80. Can 82 includes lower opening 74 so as to expose at least a portion of the membrane 60. In such an embodiment, membrane 60 comprises a conductive membrane such as palladium foil, iron titanium foil and iron magnesium foil, among others.

Alternatively, FIG. 8 illustrates a similar embodiment of the present invention as that shown in FIG. 7, configured so that membrane 60 is not required to be conductive. Specifically, FIG. 8 shows the same embodiment as in FIG. 7, with outer casing assembly 70 having cap 80, can 82 and isolation grommet 84, along with having cell 62 enclosed inside assembly 70, and membrane 60 associated just below lower opening 74. However, the device in FIG. 8 additionally includes conductive ring 86 associated between bottom of cell 62 and membrane 60. As can be seen, ring 86 connects the bottom of cell 62 with can 82, providing a conductive connection. Therefore, even if membrane 60 is not conductive, ring 86 provides a conductive path to complete a circuit for operation.

In operation, the above-described device may be placed into any of a number of devices requiring hydrogen evolution for operation. These devices, including several that will be described further herein, connect the anode 20 and the cathode 30 subassemblies of the present invention electrically, activating the zinc-air cell 62 contained within. Once activated, zinc-air cell begins producing hydrogen at a measured rate, which then passes out of the cell 62 through the non-porous cathode 36 and separator 38, if necessary, and then through the at least one aperture 34, to the outside device. Simultaneous to this process, cathode 36 and/or separator 38 help to prevent the influx and efflux of oxygen, $CO_2$, and/or water moisture to/from the cell 62.

Two working examples are described below.

EXAMPLE I

Figure 9:
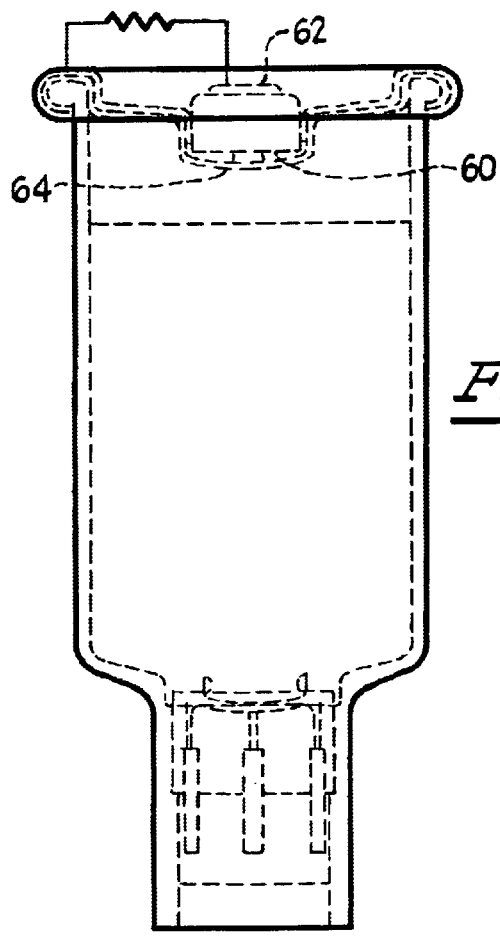
FIG. 9 shows a fluid delivery device of the present invention wherein the commercial Zn-air cell is converted into an $H_2$ generating cell.
Figure 2:
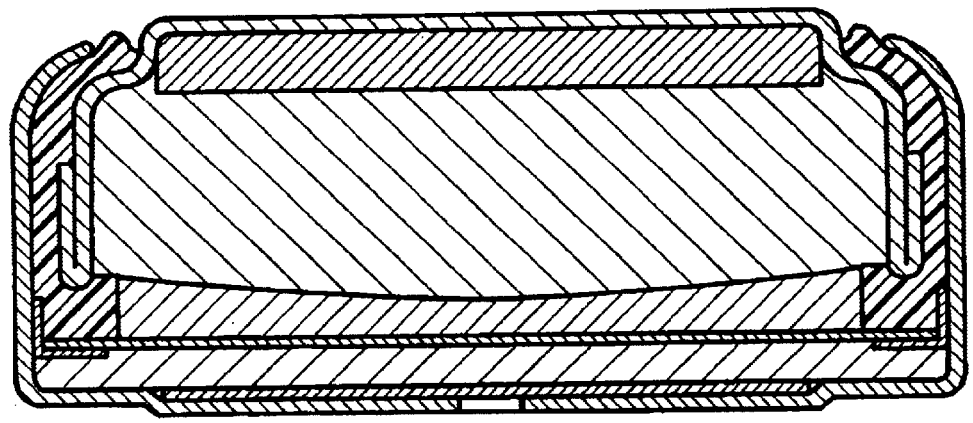
FIG. 2 is a cross-sectional view of typical prior art hydrogen generating cell.
Figure 10A:
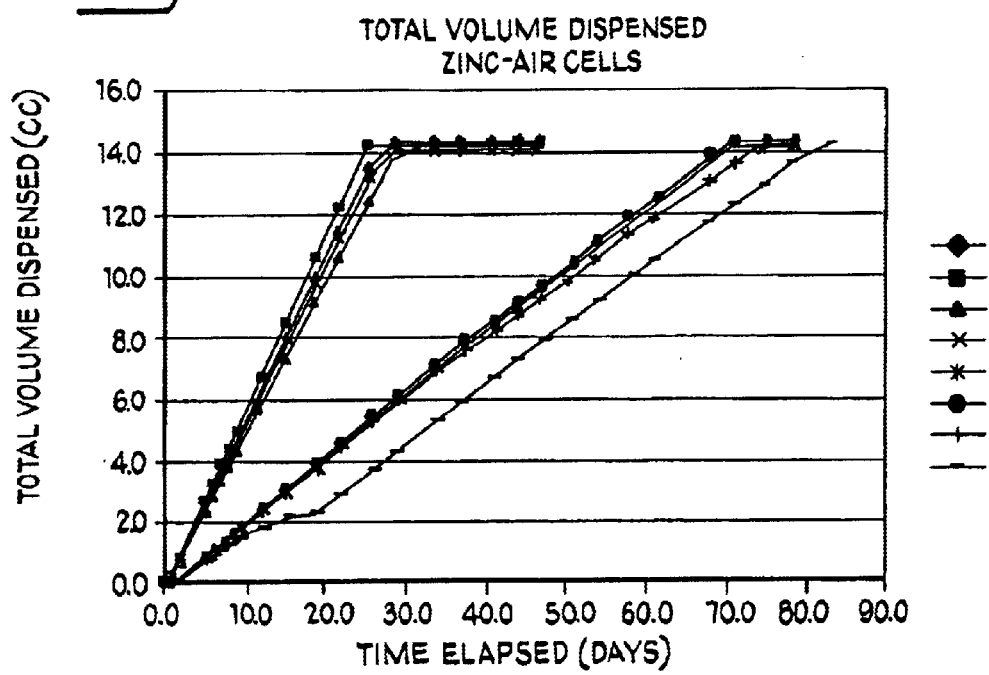
FIG. 10(a) shows the total volume of a fragrance dispensed as a function of time.
Figure 10B:
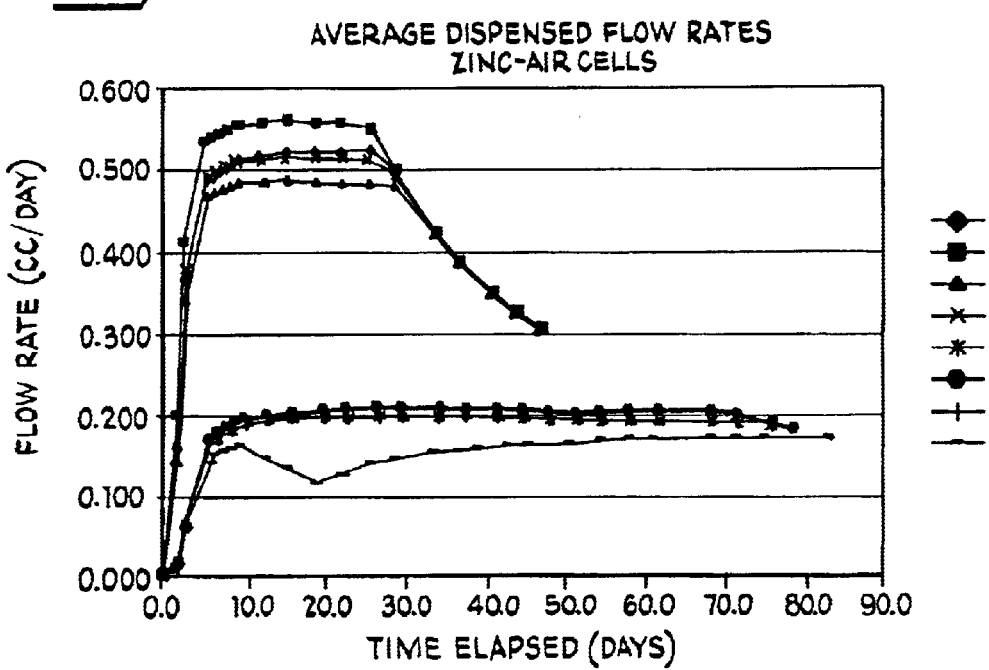
FIG. 10(b) shows the rate of dispensing as a function of time.

Commercial Zn-air cells were used as hydrogen generating cells by incorporating an hydrogen permeable but $O_2$, moisture, and $CO_2$ impermeable shield or membrane so that under shunt resistance of 4.3 kilo-ohms and 11.3 kilo-ohms, these cells generated hydrogen. Zn-air cells obtained from ENERGIZER® were used in cartridges as shown in FIG. 9. The cartridges were filled with fragrances, while the Zn-air cells were sealed in a dense non-porous polypropylene shield or membrane. A total of eight cartridges were fabricated. Four cartridges were shunted with 4.3 Kilo-ohms while four remaining cartridges were shunted with 11.3 Kilo-ohms. FIG. 10(a) shows the total volume of fragrance dispensed as a function of time, while FIG. 10(b) shows the rate of dispensing as a function of time. As one can see, the present invention, when integrated into the above device, increased the total life of cell operation, while allowing for more consistent and controlled fragrance flow.

EXAMPLE II

Figure 11A:
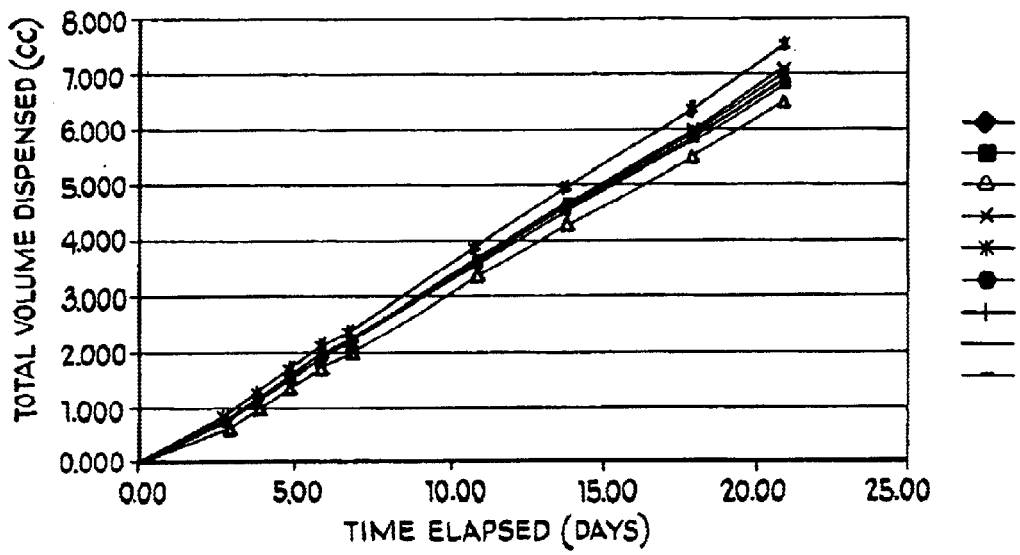
FIG. 11(a) shows the total volume of a fragrance dispensed as a function of time.
Figure 11B:
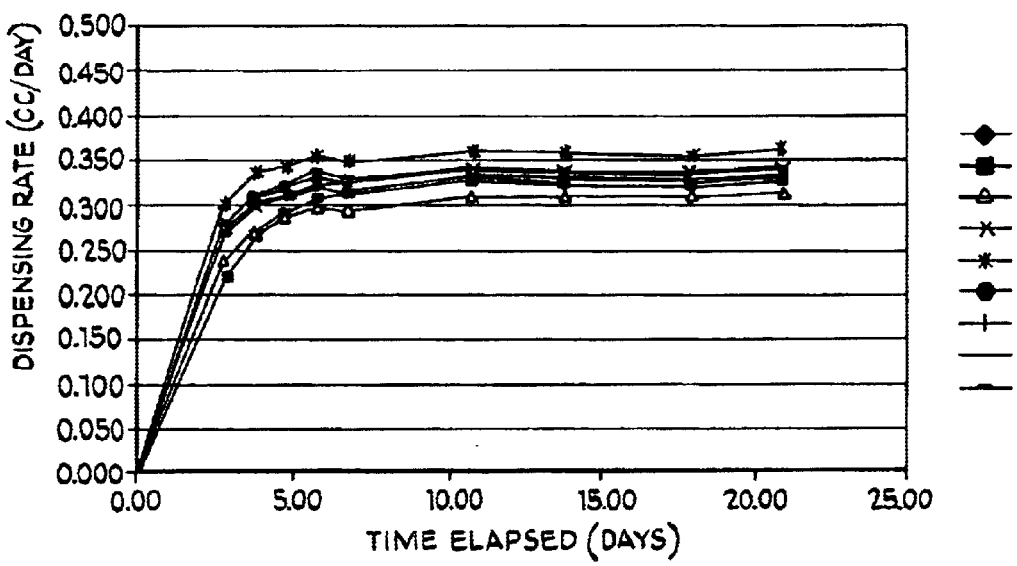
FIG. 11(b) shows the rate of dispensing as a function of time.

Graded cathode based zinc electrochemical cells were used where the cathode is non-porous. The cathode in the cell is permeable to hydrogen substantially impermeable to $O_2$, $H_2O$ and $CO_2$. The cathode is a composite of sintered PTFE and carbon sheet attached to a non-porous FEP disc. The cells were packaged in a fluid delivery cartridge with fragrance as the fluid. A total of nine cartridges were tested. FIG. 11(a) shows the total volume of fragrance dispensed as a function of time, while FIG. 11(b) shows the rate of dispensing as a function of time. The use of the graded cathode structures of the present invention enabled producible results to be obtained for both the rate of delivery and the total volume delivered over time.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A storage stable hydrogen generating galvanic cell comprising:
    an anode subassembly comprising a metal anode, electrolyte and cap;
    a cathode subassembly comprising a substantially non-porous cathode, separator and can, wherein the cathode is configured for contact with the electrolyte, the cathode being hydrogen permeable and substantially impermeable to $O_2$, $CO_2$ and water to in turn preclude the passage of $O_2$, $CO_2$ and water into and out of the cell, and to facilitate the permeation of hydrogen through at least one aperture of the can; and a grommet between at least a portion of the anode subassembly and a portion of the cathode subassembly.

2. The hydrogen generating cell of claim 1 wherein the cathode comprises at least one of a conductive non-porous polypropylene; sintered non-porous composite of carbon, PTFE, and FEP foil; palladium foil, iron titanium foil, iron magnesium foil, as well as metallic membranes of one or more of palladium, nickel, titanium, and, non-porous polymers, and composites of ceramics and palladium.

3. The hydrogen generating cell of claim 1 wherein the cathode includes a graded porosity from porous to non-porous, wherein the porous portion of the cathode faces the anode and non-porous portion of the cathode faces the aperture of the bottom can.

4. The hydrogen generating cell of claim 3 wherein the cathode comprises a combination of conductive material and polymer, wherein the ratio of conductive material to polymer may be varied within the cathode along the thickness thereof.

5. The hydrogen generating cell of claim 4 wherein the conductive material comprises at least one of graphite, active carbon, conductive ceramics, Reney nickel or other metals suitable for hydrogen generation such as for instance platinum or palladium.

6. The hydrogen generating cell of claim 1 wherein the cathode comprises a non-porous cathode, which is substantially permeable to hydrogen and substantially impermeable to $O_2$, $H_2O$, and $CO_2$.

7. The hydrogen generating cell of claim 1 wherein the at least one aperture of the cathode subassembly compromises a plurality of apertures, each of which has a diameter of more than about 2 microns.

8. The hydrogen generating cell according to claim 1 wherein the metal anode comprises a metal selected from the group consisting of zinc, lead, iron, magnesium, aluminum and mixtures and alloys thereof.

9. The hydrogen generating cell according to claim 1 wherein the anode comprises a zinc alloy.

10. A system comprising:
    a galvanic electrochemical hydrogen gas generating cell having at least one aperture in cathode subassembly can for releasing gas; and
    a membrane associated with the at least one aperture, the membrane being hydrogen permeable and substantially impermeable to $O_2$, $CO_2$ and water, to, in turn, preclude the passage of $O_2$, $CO_2$ and water into and out of the cell, and to facilitate the permeation of hydrogen through the at least one aperture of the can.

11. The system of claim 10 wherein the membrane is electrically conductive.

12. The system of claim 11 wherein the membrane is selected from the group consisting of: conductive non-porous polypropylene or Teflon; sintered composite of carbon, PTFE, and FEP foil; palladium foil, iron titanium foil, iron magnesium foil, as well as metallic membranes of one or more of palladium, nickel, titanium, and, non-porous polymers, and composites of ceramics and palladium.

13. A storage stable and efficient hydrogen generating cell comprising:
    a commercially available Zn-air cell or hydrogen generating cell comprising a porous cathode; and
    a membrane structure associated with an aperture of the cell, wherein the membrane structure is hydrogen permeable and substantially impermeable to $O_2$, $CO_2$ and water, to, in turn preclude the passage of $O_2$, $CO_2$ and water into and out of the cell, and to facilitate the permeation of hydrogen through the aperture.

14. A hydrogen generating cell of claim 13 where a membrane structure consists of packaging the cell in another enclosure comprising a non-porous membrane permeable to hydrogen but substantially impermeable to $H_2O$, $O_2$, and $CO_2$.

15. A storage-stable hydrogen-generating galvanic cell comprising:
    a cell casing including an anode portion disposed at one end of the casing and at least one aperture disposed at an opposing end of the cell casing;
    a cathode structure disposed within the casing adjacent to the aperture in the casing and electrically insulated from the anode portion of the casing, the cathode structure substantially impermeable to $O_2$, $CO_2$ and water and permeable to hydrogen; and
    an electrolyte disposed within the casing and between the cathode structure and the anode portion of the casing.

* * * * *